(12) United States Patent
Vernin (10) Patent No.: US 11,918,772 B2
(45) Date of Patent: Mar. 5, 2024

(54) FLUID SAMPLING OR INFUSION DEVICE FOR AN EXTRACORPOREAL BLOOD TREATMENT APPARATUS

(71) Applicant: GAMBRO LUNDIA AB, Lund (SE)

(72) Inventor: Guillaume Vernin, Meyzieu (FR)

(73) Assignee: Gambro Lundia AB, Lund (SE)

( * ) Notice: Subject to any disclaimer, the term of this patent is extended or adjusted under 35 U.S.C. 154(b) by 696 days.

(21) Appl. No.: 17/253,469

(22) PCT Filed: Jun. 19, 2019

(86) PCT No.: PCT/EP2019/066283
§ 371 (c)(1),
(2) Date: Dec. 17, 2020

(87) PCT Pub. No.: WO2019/243460
PCT Pub. Date: Dec. 26, 2019

(65) Prior Publication Data
US 2021/0154460 A1 May 27, 2021

(30) Foreign Application Priority Data
Jun. 19, 2018 (EP) .................................... 18178479

(51) Int. Cl.
*A61B 5/15* (2006.01)
*A61M 1/34* (2006.01)
(Continued)

(52) U.S. Cl.
CPC ... *A61M 39/0693* (2013.01); *A61B 5/150992* (2013.01); *A61M 1/342* (2013.01);
(Continued)

(58) Field of Classification Search
CPC ......... A61B 5/150992; A61B 5/15003; A61M 1/342; A61M 1/1619; A61M 2039/0202;
(Continued)

(56) References Cited

FOREIGN PATENT DOCUMENTS

| GB | 2503329 A | 12/2013 |
|---|---|---|
| WO | WO 9012606 A2 | 11/1990 |

(Continued)

OTHER PUBLICATIONS

International Search Report; International Application No. PCT/EP2019/066283 dated Dec. 9, 2019—6 Pages.
(Continued)

*Primary Examiner* — Deanna K Hall
(74) *Attorney, Agent, or Firm* — K&L Gates LLP (57) ABSTRACT

A fluid sampling or infusion device for an extracorporeal blood treatment apparatus comprises: a protective body (29) having a first aperture (30) and a second aperture (31) and comprising a connecting device (28) configured to connect, optionally in removable manner, the protective body (29) to a sampling or infusion site (20) of the extracorporeal blood treatment apparatus (1); a needle assembly (33) comprising a first end (34) connected or connectable, optionally in removable manner, to a syringe (22) and a needle (35) protruding from a second end opposite the first end (34). The needle assembly (33) is movable inside the protective body (29) between a first position and a second position. In the first position the needle (35) is completely enclosed by the protective body (29) and in the second position the needle (35) protrudes from the second aperture (31) to pierce the sampling or infusion site (20).

28 Claims, 6 Drawing Sheets

(51) Int. Cl.
    *A61M 1/36*     (2006.01)
    *A61M 39/06*     (2006.01)
    *A61M 1/16*     (2006.01)
    *A61M 5/145*     (2006.01)
    *A61M 25/00*     (2006.01)
    *A61M 39/02*     (2006.01)

(52) U.S. Cl.
    CPC .......... *A61M 1/3623* (2022.05); *A61M 1/367* (2013.01); *A61B 5/15003* (2013.01); *A61M 1/1619* (2014.02); *A61M 5/1452* (2013.01); *A61M 25/0097* (2013.01); *A61M 2039/0202* (2013.01); *A61M 2039/0205* (2013.01); *A61M 2039/0258* (2013.01)

(58) Field of Classification Search
    CPC .. A61M 2039/0258; A61M 2039/0205; A61M 1/367
    See application file for complete search history.

(56) References Cited

FOREIGN PATENT DOCUMENTS

| | | |
|---|---|---|
| WO | WO 9012606 A3 | 10/1992 |
| WO | WO 2008101025 A1 | 8/2008 |
| WO | WO 2015181234 A1 | 12/2015 |

OTHER PUBLICATIONS

Written Opinion of the International Searching Authority; International Application No. PCT/EP2019/066283 dated Dec. 9, 2019—7 Pages.

Extended European Search Report; EP Application No. 18178479.4; report dated Dec. 19, 2018—7 Pages.

FLUID SAMPLING OR INFUSION DEVICE FOR AN EXTRACORPOREAL BLOOD TREATMENT APPARATUS

PRIORITY CLAIM

The present application is a National Phase of International Application No. PCT/EP2019/066283, filed Jun. 19, 2019, which claims priority to EP Application No. 18178479.4, filed Jun. 19, 2018. The entire contents of each are incorporated herein by reference and relied upon.

FIELD OF THE INVENTION

The present invention relates to a fluid sampling or infusion device for an extracorporeal blood treatment apparatus. Extracorporeal blood treatment involves removing blood from a patient, treating the blood externally to the patient, and returning the treated blood to the patient. Extracorporeal blood treatment is typically used to extract undesirable matter or molecules from the patient's blood and/or to add desirable matter or molecules to the blood. Extracorporeal blood treatment is used with patients unable to effectively remove matter from their blood, such as when a patient has suffered temporary or permanent kidney failure. These patients and other patients may undergo extracorporeal blood treatment to add or remove matter to their blood, to maintain an acid/base balance or to remove excess body fluids, for example.

Extracorporeal blood treatment is typically accomplished by removing the blood from the patient in e.g. a continuous flow, introducing the blood into a primary chamber, also referred to as blood chamber, of a treatment unit (such as a dialyzer or an hemo-filter) where the blood is allowed to flow past a semi-permeable membrane. The semi-permeable membrane selectively allows matter in the blood to cross the membrane from the primary chamber into a secondary chamber and also selectively allows matter in the secondary chamber to cross the membrane into the blood in the primary chamber, depending on the type of treatment.

A number of different types of extracorporeal blood treatments may be performed. In an ultrafiltration (UF) treatment, undesirable fluid is removed from the blood by convection across the membrane into the secondary chamber. In a hemofiltration (HF) treatment, the blood flows past the semipermeable membrane as in UF (where waste and undesirable fluid are removed) and desirable matter is added to the blood, typically by dispensing a fluid into the blood either before and/or after it passes through the treatment unit and before it is returned to the patient. In a hemodialysis (HD) treatment, a secondary fluid containing desirable matter is introduced into the secondary chamber of the treatment unit. Undesirable matter from the blood crosses the semi-permeable membrane into the secondary fluid by diffusion and desirable matter from the secondary fluid crosses the membrane into the blood. In a hemodiafiltration (HDF) treatment, blood and secondary fluid exchange matter as in HD, and, in addition, matter is added to the blood, typically by dispensing a fluid into the treated blood (infusion) either before and/or after it passes through the treatment unit and before its return to the patient as in HF. For example, an anticoagulant, like heparin or citrate, may be infused in the access line. In an adsorption treatments, components with a pathophysiological potential, such as protein-bound toxins, are removed from blood through adsorber cartridges.

BACKGROUND

Sampling of blood or other fluids from the extracorporeal blood treatment apparatus during treatment of a patient is performed in order to monitor blood and/or other fluid composition and/or parameters.

Today this need gets higher focus with the development of the citrate anticoagulation mode that requires more frequent sampling than other anticoagulation strategies.

Infusion of fluids in the extracorporeal blood treatment apparatus during treatment of a patient or between two blood sampling procedures (flushing step comprising rapid infusion of saline to wash) are also performed.

In accordance with known solutions, needleless sampling or infusion sites have been used like, e.g., a T connector ended by female Luer, a septum compatible with a plastic cannula, a needless valve, a needless access port which may be accessed through a Luer syringe.

These kind of sampling or infusion sites may lead to clots generation due to the presence of internal stagnation areas.

Septa that are to be punctured with sharp needles are also known. The use of sharp needles may create hazardous situations for the user during sampling or infusion.

Prior art document U.S. Pat. No. 5,495,855 discloses a protective shield for a blood sampling unit that is movably engaged to an adapter having a needle attached. The shield attaches to a tube holder when the needle is covered by the shield. Longitudinal grooves on the adapter guide the shield between a first position, covering the needle, and a second position, exposing the needle. The shield can be locked in either the first position or the second position. The blood sampling unit is safely disassembled or reassembled when the needle is covered by the shield.

SUMMARY OF THE INVENTION

In view of the above, it is an object of embodiments of the present invention to propose a fluid sampling or infusion device which interfaces between the sampling or infusion site of an extracorporeal blood treatment apparatus and a syringe and allows simple, quick, easy and safe fluid sampling or infusion.

It is an object of embodiments of the present invention to propose a fluid sampling or infusion device using a needle to pierce a tube or a self-sealing septum at the sampling or infusion zone.

It is a further object of embodiments of the present invention to propose a fluid sampling or infusion device which is safe and able to protect the user from the sharp edge of the needle at all times during the sampling or infusion process.

It is a further object of embodiments of the present invention to propose a fluid sampling or infusion device which is compatible with a plurality of sampling or infusion sites.

It is a further object of embodiments of the present invention to propose a fluid sampling or infusion device which does not require sampling or infusion sites of particular shape and size and thus avoids clotting risks.

It is a further object of embodiments of the present invention to propose a fluid sampling or infusion device which allows using standard syringes.

It is a further object of embodiments of the present invention to propose a fluid sampling or infusion device which may be disposable.

At least one of the above objects is substantially achieved by a fluid sampling or infusion device particularly for an extracorporeal blood treatment apparatus, wherein the fluid sampling or infusion device comprises a needle protected by a shield or a protective body which is configured to be connected to a sampling or infusion zone of e.g., the extracorporeal blood apparatus and to a syringe.

Aspects of the invention are disclosed in the following.

In accordance with a $1^{st}$ independent aspect, a fluid sampling or infusion device, in particular for an extracorporeal blood treatment apparatus, comprises:
- a protective body having a first aperture and a second aperture and comprising a connecting device configured to connect the protective body to a sampling or infusion site particularly of the extracorporeal blood treatment apparatus;
- a needle assembly comprising a first end connectable to a syringe and a needle protruding from a second end opposite the first end;
- wherein at least the needle of the needle assembly is movable inside the protective body at least between a first position and a second position;

wherein in the first position the needle is completely enclosed by the protective body;

wherein in the second position at least part of the needle protrudes from the second aperture of the protective body to allow piercing the sampling or infusion site.

The fluid sampling or infusion device allows to perform sampling or infusion while the needle is always hidden and protected from user contact inside the protective body, before, during and after sampling or infusion, i.e. when the needle is in the first position or in the second position. Furthermore, the fluid sampling or infusion device is compatible with a plurality of sampling or infusion sites.

In a $2^{nd}$ independent aspect, a fluid sampling or infusion assembly for extracorporeal blood treatment apparatus comprises:
- the fluid sampling or infusion device of aspect 1 or of one of the following aspects;
- a sampling or infusion site comprising a stretch of tubing in fluid connection with the extracorporeal blood treatment apparatus or part of the extracorporeal blood treatment apparatus.

The sampling or infusion site includes an inlet and an outlet for the fluid, in detail blood, and a channel fluidly connecting inlet and outlet; a side access is present and provides for an access to the channel. In one exemplary embodiment, the inlet receives internally an end portion of a fluid (e.g., blood) inlet tube and the outlet receives internally an end portion of a fluid (e.g., blood) outlet tube.

In a $3^{rd}$ aspect according aspect 2, the sampling or infusion site comprises at least a part, optionally a tab, optionally a plurality of parts or tabs, configured to be engaged by the connecting device.

The connecting device allows to attach the fluid sampling or infusion device to the extracorporeal blood treatment apparatus onto the sampling or infusion site only when sampling or infusion is needed.

In a $4^{th}$ aspect according aspect 1, 2 or 3, the tabs protrudes laterally from the stretch of tubing.

In a $5^{th}$ aspect according to any of aspects 1 to 4, the sampling or infusion site comprises the stretch of tubing and a septum closing a side access to the stretch of tubing and configured to be pierced by the needle of the fluid sampling or infusion device, optionally the septum is made of self-sealing material.

In a $6^{th}$ aspect according to aspect 5, the sampling or infusion site comprises a cap surrounding the septum and configured to be engaged by the second aperture of the protective body when the connecting device of the protective body is connected to the sampling or infusion site.

In a $7^{th}$ aspect according to any of aspects 1 to 6, the connecting device is a clip fastener. Thanks to the clip fastener, connection and disconnection are quick and easy.

In an $8^{th}$ aspect according to any of aspects 1 to 7, the connecting device comprises elastic arms protruding from the protective body and configured to engage tab or tabs of the sampling or infusion site.

In a $9^{th}$ aspect according to aspect 2 or any of aspects 3 to 8 when according to aspect 2, the fluid sampling or infusion assembly comprises a syringe having a tip connected or connectable to the first end of the needle assembly.

In a $10^{th}$ aspect according to any of aspects 1 to 9, the first end of the needle assembly is connected or connectable to the syringe in removable manner.

In an $11^{th}$ aspect according to any of aspects 1 to 10, the whole needle assembly is movable inside the protective body at least between the first position and the second position.

In a $12^{th}$ aspect according to any of aspects 1 to 11, the protective body has a main axis and the needle is movable along the main axis between the first position and the second position.

In a $13^{th}$ aspect according to any of aspects 1 to 12, the protective body is a cylindrical housing.

In a $14^{th}$ aspect according to any of aspects 1 to 13, at least in the first position, the first end of the needle assembly protrudes from the first aperture of the protective body.

In a $15^{th}$ aspect according to any of aspects 1 to 16, in the second position, the first end of the needle assembly is placed inside the protective body.

In a $16^{th}$ aspect according to any of aspects 1 to 15, the device comprises a first blocker operatively interposed between the needle assembly and the protective body and placed close to the first aperture, wherein the first blocker is configured to block the needle assembly in the first position.

The first blocker holds the needle inside the protective body when sampling or infusion is not performed and prevents that pushing the needle assembly may cause extraction of the needle.

In a 17th aspect according to aspect 16, in the first position, the needle assembly is movable with respect to the first blocker between a first angular position and a second angular position.

In a $18^{th}$ aspect according to aspect 17, in the first angular position the first blocker prevents an axial displacement of the needle assembly.

In a $19^{th}$ aspect according to aspect 17 or 18, in the second angular position the first blocker allows an axial displacement of the needle assembly towards the second aperture.

In a $20^{th}$ aspect according to any of aspects 17 to 19, when the needle assembly is in the first angular position, the first blocker is configured to prevent a further clockwise rotation of the needle assembly and, optionally, when the needle assembly is in the second angular position, the first blocker is configured to prevent a further counter clockwise rotation of the needle assembly.

In a $21^{st}$ aspect according to any of aspects 14 to 19, when the needle assembly is in the first angular position, the first blocker is configured to prevent a further counter clockwise rotation of the needle assembly and, optionally, when the needle assembly is in the second angular position, the first blocker is configured to prevent a further clockwise rotation of the needle assembly.

This way, the syringe may be screwed and unscrewed onto/from the first end of the needle assembly while said first end is stationary.

In a 22$^{nd}$ aspect according to any of aspects 14 to 21, the first blocker comprises at least one first relief protruding radially inside the protective body, optionally the first relief is arch shaped, optionally the first blocker comprises a plurality of first relieves, optionally three first relieves, protruding radially inside the protective body and angularly spaced from each other.

In a 23$^{rd}$ aspect according to any of aspects 17 to 21, the first blocker comprises an annular surface facing the first relief and spaced from said first relief to accommodate between said annular surface and the first relief a portion of the needle assembly, optionally a lug of the needle assembly; wherein, optionally, the annular surface is an internal surface of the protective body and optionally surrounds the first aperture of said protective body.

In a 24$^{th}$ aspect according to aspect 22 or 23, the first relief comprises a first stop surface perpendicular to an axial direction of movement of the needle assembly and a second stop surface perpendicular to a circumferential direction of the needle assembly.

In a 25$^{th}$ aspect according to any of aspects 1 to 24, the device comprises a second blocker operatively interposed between the needle assembly and the protective body and spaced from the first aperture, wherein the second blocker is configured to block the needle assembly in the second position.

The second blocker allows the user to pull the plunger of the syringe to extract a fluid sample while the needle is stationary inside the sampling or infusion site.

In a 26$^{th}$ aspect according to aspect 25, in the second position, the needle assembly is movable with respect to the second blocker between a first angular position and a second angular position.

In a 27$^{th}$ aspect according to aspect 26, in the first angular position the second blocker prevents an axial displacement of the needle assembly towards the first aperture.

In a 28$^{th}$ aspect according to aspect 25 or 26, in the second angular position the second blocker allows an axial displacement of the needle assembly towards the first aperture.

In a 29$^{th}$ aspect according to aspect 26, 27 or 28, when the needle assembly is in the first angular position, the second blocker is configured to prevent a further clockwise rotation of the needle assembly and optionally when the needle assembly is in the second angular position, the second blocker is configured to prevent a further counter clockwise rotation of the needle assembly.

In a 30$^{th}$ aspect according to any of aspects 26 to 28, when the needle assembly is in the first angular position, the second blocker is configured to prevent a further counter clockwise rotation of the needle assembly and optionally when the needle assembly is in the second angular position, the second blocker is configured to prevent a further clockwise rotation of the needle assembly.

In a 31$^{st}$ aspect according to the previous aspect, the second blocker comprises at least one second relief protruding radially inside the protective body, optionally the second relief is arch shaped.

In a 32$^{nd}$ aspect according to any of the previous aspects 26 to 31, the second blocker comprises a plurality of second relieves, optionally three second relieves, protruding radially inside the protective body and angularly spaced from each other.

In a 33$^{rd}$ aspect according to aspect 31 or 32, the second relief comprises a first stop surface perpendicular to an axial direction of movement of the needle assembly and a second stop surface perpendicular to a circumferential direction of the needle assembly.

In a 34$^{th}$ aspect according to any of aspects 1 to 33, the needle assembly comprises at least one lug projecting radially outward and configured to engage the first blocker or the second blocker, optionally the second relief is arch shaped.

In a 35$^{th}$ aspect according to any of aspects 1 to 34, the needle assembly comprises a plurality of lugs projecting radially outward and angularly spaced from each other.

In a 36$^{th}$ aspect according to aspect 34 or 35, the lug is shaped to pass between two first relieves or between two second relieves.

In a 37$^{th}$ aspect according to any of aspects 1 to 36, the device comprises a mechanism for automated needle retraction from the second position towards the first position.

In a 38$^{th}$ aspect according to previous aspect 37, the mechanism comprises a spring, optionally a helical spring, operatively interposed between the protective body and the needle assembly and configured to push the needle assembly towards the first position.

This way, after sampling or infusion, the needle is retracted inside the protective body.

In a 39$^{th}$ aspect according to any of aspects 1 to 38, the protective body comprises an interior wall placed close to the second aperture and having a through passage for the needle.

In a 40$^{th}$ aspect according to aspect 39 when according to aspect 38, the spring has a first extremity placed against the interior wall and a second extremity placed against the needle assembly.

In a 41$^{st}$ aspect according to aspect 38 or 40, the spring surrounds the needle, optionally the needle is coaxial to the spring.

In a 42$^{nd}$ aspect according to any of aspects 1 to 41, the first end of the needle assembly has a thread configured to engage a thread of a tip of the syringe.

In a 43$^{rd}$ aspect according to any of aspects 1 to 42, the syringe has a male Luer tip.

In a 44$^{th}$ aspect according to any of aspects 1 to 43, the tip of the syringe comprises an inner threaded cylindrical body and a conical end placed inside the inner threaded cylindrical body and provided with a syringe opening.

In a 45$^{th}$ aspect according to any of aspects 1 to 44, the needle assembly comprises a tubular body having the first end.

In a 46$^{th}$ aspect according to any of aspect 1 to 45, the first end of the needle assembly has an external thread configured to engage a thread of a tip of the syringe; optionally a conical end of the tip of the syringe is configured to enter a through passage in the first end.

In a 47$^{th}$ aspect according to any of aspect 1 to 46, the first end of the needle assembly is a female Luer, optionally the needle assembly is a female Luer lock.

In a 48$^{th}$ aspect according to aspect 47, a proximal end of the needle is mounted inside the tubular body and at least a distal tip of the needle protrudes from the tubular body.

In a 49$^{th}$ aspect according to aspect 48, the needle assembly comprises a valve mounted inside the tubular body and placed at the proximal end of the needle.

In a 50$^{th}$ aspect according to aspect 49, the valve is a swabable valve.

In a 51$^{st}$ aspect according to aspect 49 or 50, the needle assembly comprises a transverse wall placed inside the tubular body and having a hole; optionally the valve is accommodated between the transverse wall and the first end of the needle assembly to open or close the hole.

In a 52$^{nd}$ aspect according to aspect 51, the proximal end of the needle is joined to the transverse wall and in fluid communication with the hole.

In a 53$^{rd}$ aspect, an extracorporeal blood treatment apparatus comprises at least one sampling or infusion site and at least a fluid sampling or infusion device according to at least one of the present aspects.

In a 54$^{th}$ aspect according to aspect 53, the extracorporeal blood treatment apparatus comprises a blood treatment device and a fluid circuit; wherein the fluid circuit comprises: an extracorporeal blood circuit coupled to the blood treatment device and configured to be coupled to vascular accesses of the patient, a blood pump configured to be coupled to a pump section of the extracorporeal blood circuit; optionally, a treatment fluid circuit operatively connected to the extracorporeal blood circuit and at least a fluid pump configured to be coupled to the treatment fluid circuit; optionally an infusion circuit operatively connected to the extracorporeal blood circuit and at least an infusion pump configured to be coupled to the infusion fluid circuit.

In a 55$^{th}$ aspect according to aspect 54, the sampling or infusion site is located on the blood circuit, optionally on a blood withdrawal line and/or on a blood return line of the blood circuit.

In a 56$^{th}$ aspect according to aspect 55, the sampling or infusion site is located upstream and/or downstream of an infusion port on the blood withdrawal line.

In a 57$^{th}$ aspect according to any of aspects 54 to 56, the sampling or infusion site is located on the blood return line and downstream of a warmer connection.

In a 58$^{th}$ aspect according to any of aspects 54 to 57, the treatment fluid circuit comprises an effluent line connected to the blood treatment device and the sampling or infusion site is located on the effluent line.

In a 59$^{th}$ aspect according to any of aspects 1 to 58, the fluid sampling or infusion device is disposable.

In a 60$^{th}$ aspect, a fluid sampling or infusion method performed using the fluid sampling or infusion device or the fluid sampling or infusion assembly of one or more of the previous aspects, comprises:
  connecting the fluid sampling or infusion device to the sampling or infusion site through the connecting device;
  connecting the syringe to the first end of the needle assembly while the needle assembly is in the first position;
  pushing the syringe and the needle assembly towards the second position to pierce the sampling or infusion site;
  extracting a fluid sample or injecting a fluid through the syringe.

In a 61$^{st}$ aspect according to aspect 60, the method further comprises:
  releasing the syringe and the needle assembly from the second position to extract the needle from the sampling or infusion site;
  disconnecting the fluid sampling or infusion device from the sampling or infusion site.

In a 62$^{nd}$ aspect according to aspect 60 or 61 when aspect 60 is according to any of aspects 17 to 24, connecting the syringe to the first end of the needle assembly comprises screwing the needle tip on the first end while the needle assembly is in the first angular position.

In a 63$^{rd}$ aspect according to aspect 62, before pushing the syringe and the needle assembly towards the second position, the needle assembly is moved to the second angular position.

In a 64$^{th}$ aspect according to aspect 60 or 61 when aspect 60 is according to any of aspects 26 to 33, when the syringe and the needle assembly reach the second position, the needle assembly is moved to the first angular position.

In a 65$^{th}$ aspect according to aspect 61 when aspect 60 is according to aspect 37, releasing the syringe and the needle assembly from the second position is performed by the mechanism for automated needle retraction.

In a 66$^{th}$ aspect according to anyone of the previous aspects, the sampling or infusion site has axially aligned inlet and outlet for the fluid, the side access defining an access to a channel fluidly connecting inlet and outlet, the access being transversal to a longitudinal development of the channel.

In a 67$^{th}$ aspect according to anyone of the previous aspects, the sampling or infusion site is made of a material more rigid than the material of the flexible tubes conveying the fluid towards the inlet and away from the outlet.

In a 68$^{th}$ aspect according to anyone of the previous aspects, the sampling or infusion site is monolithic.

In a 69$^{th}$ independent aspect, an extracorporeal blood treatment set is provided comprising:
  the fluid sampling or infusion device of anyone of the previous fluid sampling or infusion device aspects;
  a blood treatment unit including a semipermeable membrane dividing the unit into a blood and a fluid chamber;
  a blood withdrawal line configured for connection to a patient vascular access and connected to an inlet port of the blood chamber;
  a blood return line configured for connection to a patient vascular access and connected to an outlet port of the blood chamber;
  at least one sampling or infusion site comprising a stretch of tubing mounted and in fluid communication with the blood withdrawal line or the blood return line.

In a 70$^{th}$ aspect according to the previous aspect, the extracorporeal blood treatment set is a disposable set.

The sampling or infusion site of the extracorporeal blood treatment set being in accordance with anyone of the characteristics previously described.

DESCRIPTION OF THE DRAWINGS

The following drawings relating to aspects of the invention are provided by way of non-limiting example.

DETAILED DESCRIPTION

Figure 1:
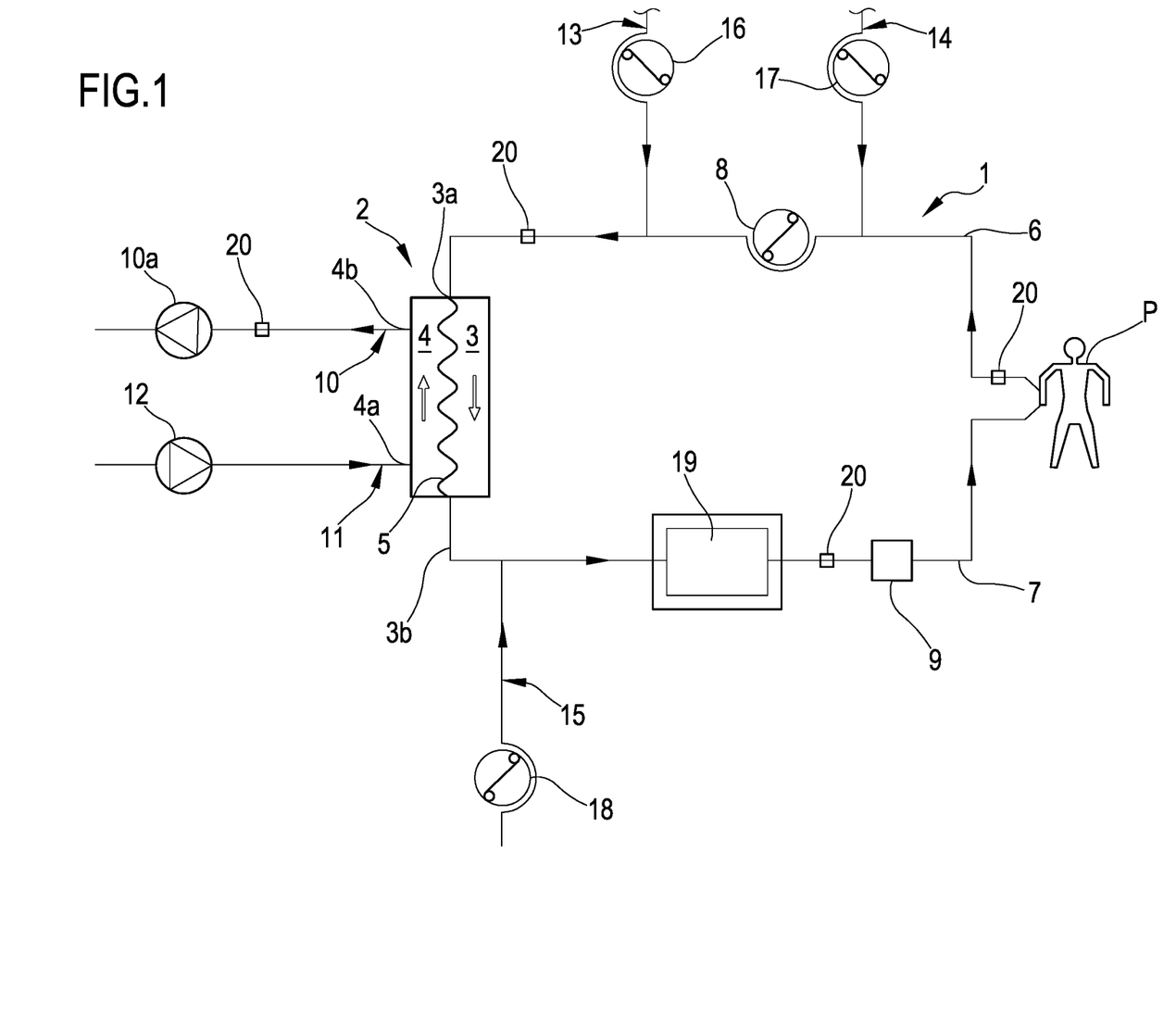
FIG. 1 shows a schematic representation of an extracorporeal blood treatment apparatus provided with a plurality of sampling or infusion sites.

With reference to the appended drawings, FIG. 1 shows a schematic representation of an extracorporeal blood treatment apparatus 1.

The apparatus 1 comprises one blood treatment device 2, for example a hemofilter, a hemodiafilter, a plasmafilter, a dialysis filter or other unit suitable for processing the blood taken from a patient P.

The blood treatment device 2 has a first compartment or blood chamber 3 and a second compartment or fluid chamber 4 separated from one another by a semipermeable membrane 5. A blood withdrawal line 6 is connected to an inlet port 3a of the blood chamber 3 and is configured, in an operative condition of connection to the patient P, to remove blood from a vascular access device inserted, for example in a fistula on the patient P. A blood return line 7 connected to an outlet port 3b of the blood chamber 3 is configured to receive treated blood from the treatment unit 2 and to return the treated blood, e.g. to a further vascular access also connected to the fistula of the patient P. Note that various configurations for the vascular access device may be envisaged: for example, typical access devices include a needle or catheter inserted into a vascular access which may be a fistula, a graft or a central (e.g. jugular vein) or peripheral vein (femoral vein) and so on. The blood withdrawal line 6 and the blood return line 7 are part of an extracorporeal blood circuit of the apparatus 1.

The extracorporeal blood circuit 6, 7 and the treatment unit 2 are usually disposable parts which are loaded onto a frame of a blood treatment machine, not shown.

As shown in FIG. 1, the apparatus 1 comprises at least a first actuator, in the present example a blood pump 8, which is part of said machine and operates at the blood withdrawal line 6, to cause movement of the blood removed from the patient P from a first end of the withdrawal line 6 connected to the patient P to the blood chamber 3. The blood pump 8 is, for example, a peristaltic pump, as shown in FIG. 1, which acts on a respective pump section of the withdrawal line 6 (see the arrows in FIG. 1 indicative of the blood flow along the blood withdrawal line 6).

It should be noted that for the purposes of the present description and the appended claims, the terms "upstream" and "downstream" may be used with reference to the relative positions taken by components belonging to or operating on the extracorporeal blood circuit. These terms are to be understood with reference to a blood flow direction from the first end of the blood withdrawal line 6 connected to the patient P towards the blood chamber 3 and then from the blood chamber 3 towards a second end of the blood return line 7 connected to the vascular access of the patient P.

The apparatus 1 may further comprise an air trapping device 9 operating on the blood return line 7 (the air trapping device 9 is a venous deaeration chamber). The air trapping device 9 is placed online in the blood return line 7.

A first section of the blood return line 7 puts in fluid communication the outlet port 3b of the blood chamber 3 with the air trapping device 9 and a second section of the blood return line 7 puts in fluid communication the air trapping device 9 with the patient P. The blood coming from the blood chamber 3 of the treatment device 2 enters and exits the air trapping device 9 before reaching the patient P.

The apparatus 1 of FIG. 1 further comprises one fluid effluent line 10 connected with an outlet port 4b of the fluid chamber 4 such as to receive the filtered waste fluid through the semipermeable membrane 5. The fluid effluent line 10 receives such filtered waste fluid coming from the fluid chamber 4 of the treatment device 2, for example, comprising used dialysis liquid and/or liquid ultra-filtered through the membrane 5. The fluid effluent line 10 leads to a receiving element, not shown, for example having a collection bag or a drainage pipe for the waste fluid. A dialysate pump 10A may operate on the fluid effluent line 10.

In the example of FIG. 1, a dialysis line 11 is also present for supplying a fresh treatment fluid into the inlet port 4a of the fluid chamber 4. The presence of this dialysis line 11 is not strictly necessary since, in the absence of the dialysis line 11, the apparatus 1 is still able to perform treatments such as ultrafiltration, hemofiltration or plasma-filtration. In case the dialysis line 11 is present, a fluid flow intercept device may be used, not shown, to selectively allow or inhibit fluid passage through the dialysis line 11, depending on whether or not a purification by diffusive effect is to be performed inside the treatment device 2.

The dialysis line 11, if present, is typically equipped with a dialysis pump 12 and is able to receive a fresh fluid from a module, not shown, for example a bag or on-line preparation section of dialysis fluid, and to send such a fluid to the inlet port 4a of the fluid chamber 4.

The fluid effluent line 10, the dialysis line 11 and the fluid chamber 4 are part of a treatment fluid circuit.

The apparatus 1 as shown in FIG. 1 further comprises an infusion circuit comprising one or more infusion lines of a replacement fluid. According to the embodiment of FIG. 1, a pre-infusion line 13 is connected to the blood withdrawal line 6 between the blood pump 8 and the inlet port 3a of the blood chamber 3. A pre pump infusion line 14 is connected to the blood withdrawal line 6 upstream of the blood pump 8, between said blood pump 8 and the vascular access device inserted in the fistula on the patient P. A post-infusion line 15 is connected to the blood return line 7 upstream of the air trapping device 9. Each of the pre- and/or post-infusion lines 13, 14, 15 are provided with a respective pump 16, 17, 18. The pre- and/or post-infusion lines 13, 14, 15 may be supplied by fluid coming from bags or directly by infusion fluid prepared on-line. Each of the pre- and/or post-infusion lines 13, 14, 15 are part of the treatment fluid circuit.

The blood return line 7 presents a heated portion 19 configured to be connected to a warmer in which blood is warmed before flowing into the blood circulation system of the patient P.

The extracorporeal blood treatment apparatus 1 comprises one or more sampling or infusion sites 20 configured to allow extraction of samples of blood or other fluid or injection of fluids through a fluid sampling or infusion device 21 and a syringe 22. In the embodiment of FIG. 1, one sampling or infusion site 20 is located on the blood withdrawal line 6 upstream of an infusion port of the pre pump infusion line 14; one sampling or infusion site 20 is located on the blood withdrawal line 6 downstream of the blood pump 8; one sampling or infusion site 20 is located on the blood return line 7 and downstream of the heated portion 19; one sampling or infusion site 20 is located on the effluent line 10 and upstream of the dialysate pump 10A.

One of the sampling or infusion sites 20 will be described in the following.

The sampling or infusion site 20 comprises (FIG. 2) a body forming a through passage delimiting a stretch of tubing or conduit or channel 23 in fluid connection with extracorporeal blood treatment apparatus 1. The through passage is connected to and part of the respective fluid line (blood withdrawal line 6, blood return line 7, fluid effluent line 10). Opposite ends (axially aligned inlet and outlet) of the through passage are connected to tubes of the respective fluid line. The sampling or infusion site 20 of the embodiment shown in the attached figures is monolithic and is made of a material more rigid than the material of the flexible tubes conveying the fluid towards the inlet and away from the outlet.

A septum 24 in the body of the sampling or infusion site 20 (FIGS. 6, 7 and 8) closes a side access 25 to the stretch of tubing 23. The side access 25 is transversal to a longitudinal development of the channel. The septum may be made of self-sealing material (e.g. silicone or thermoplastic elastomer like SEBS) so that a needle may pierce it and the septum closes again once the needle is removed. The septum 24 is fitted into the side access and it is hold in place by a cap 26. The body of the sampling or infusion site 20 further comprises tabs 27 having edges protruding laterally from the stretch of tubing 23 and configured to be engaged by the fluid sampling or infusion device 21. The sampling or infusion site 20 shown in the attached figures comprises four tabs 27 defined by corners of a plate which is part of said sampling or infusion site.

The fluid sampling or infusion device 21 may be connected or disconnected to the sampling or infusion site 20 through a connecting device 28 which is part of said fluid sampling or infusion device 21 and which may be coupled in removable manner to the tabs 27.

The fluid sampling or infusion device 21 comprises a protective body 29 shaped like a cylindrical housing with a main axis "X-X" and having a first aperture 30 and a second aperture 31 opposite the first aperture 30. The second aperture 31 is configured to fit onto the cap 26 of the sampling or infusion site 20 when the connecting device 28 is coupled to the tabs 27.

The connecting device is a clip fastener comprising elastic arms 32 protruding from the protective body 29 and having extremities configured to engage the tabs 27. The embodiment shown in the attached figures has four arms 32 engageable to the four corners of the plate of the sampling or infusion site 20. Each arm 32 of comprises a first portion protruding from the cylindrical housing on a plane perpendicular to the main axis "X-X" and a second portion parallel to the main axis "X-X" and carrying the extremity configured to engage the plate. Each extremity has a slanted surface to allow clipping of the fluid sampling or infusion device 21 on the sampling or infusion site 20 by snap fitting.

The fluid sampling or infusion device 21 comprises a needle assembly 33 comprising a first end 34 connectable to the syringe 22 and a needle 35 protruding from a second end opposite the first end 34.

Figure 7:
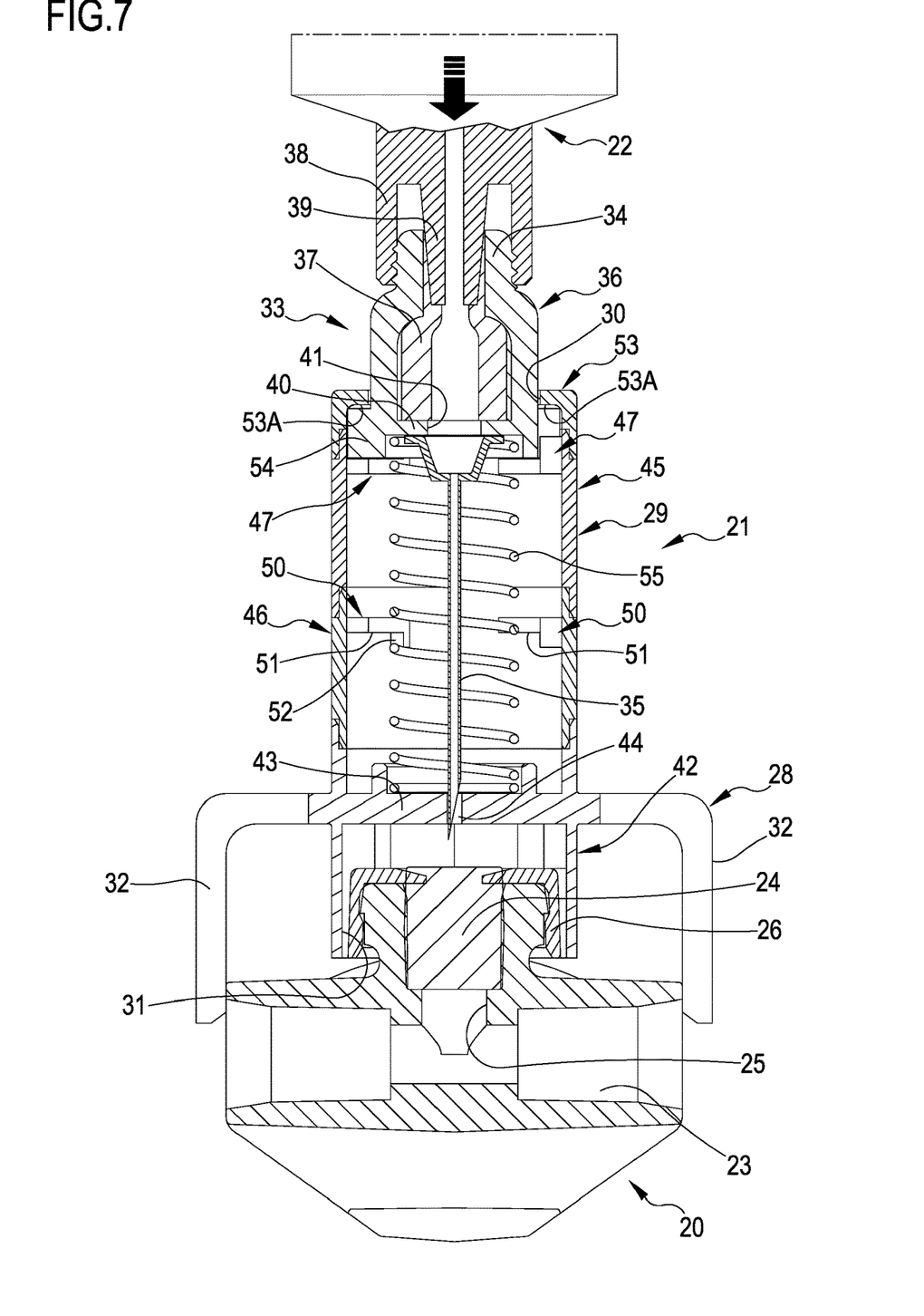
Figure 8:
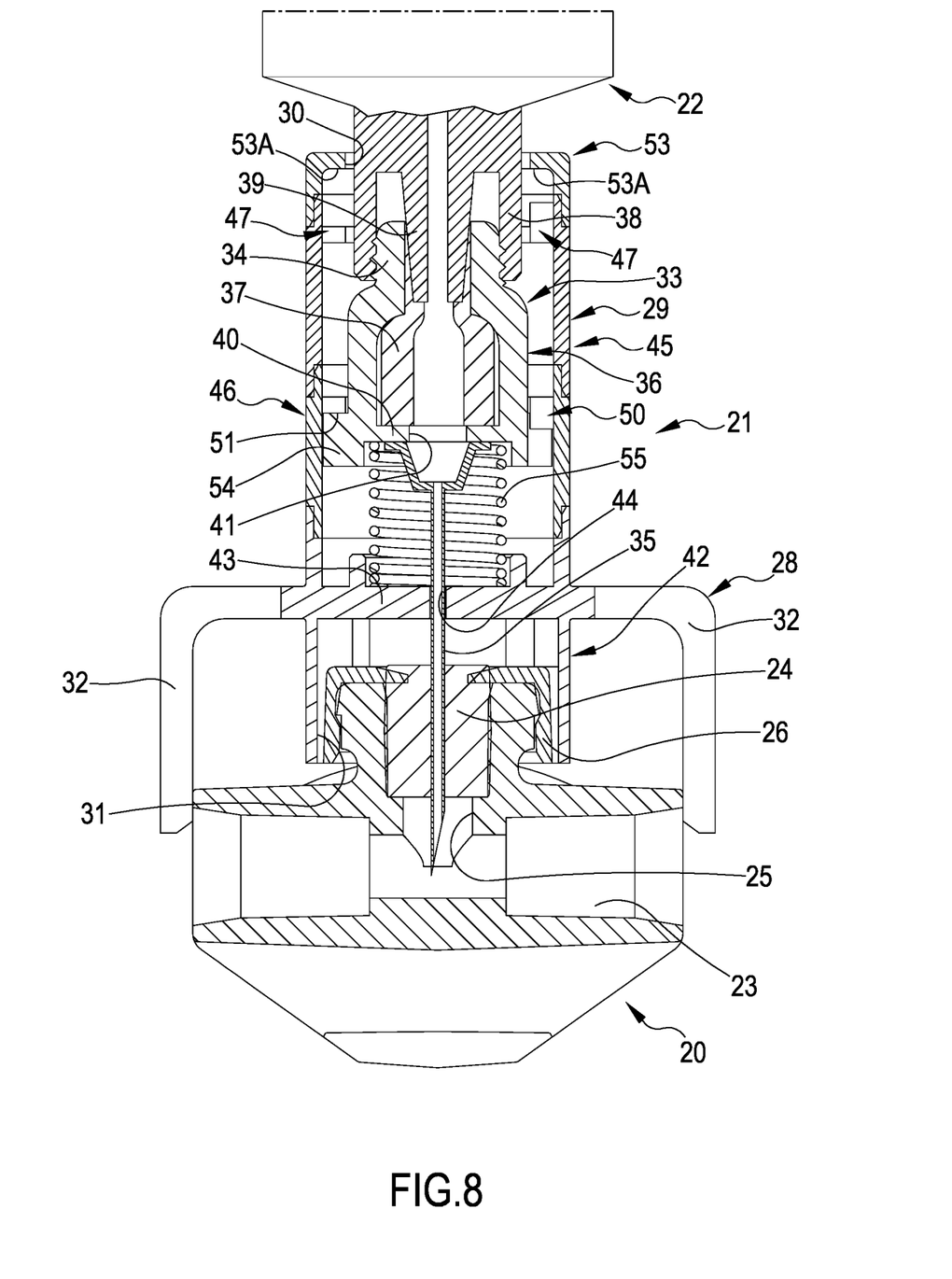

The needle assembly 33 comprises a tubular body 36 having the first end 34 and a valve 37 mounted inside the tubular body 36. The tubular body 36 is tapered towards the first end 34 and the first end 34 has a through passage and an external thread configured to engage a thread of a tip of the syringe 22. The syringe 22 comprises a barrel with a plunger, not shown in the attached drawings. The syringe 22 has a male Luer tip which comprises an inner threaded cylindrical body 38 and a conical end 39 placed coaxially inside the threaded cylindrical body 38 and provided with a syringe opening. When the inner threaded cylindrical body 38 is threaded onto the first end 34 of the needle assembly 33, the conical end 39 of the syringe 22 is accommodated into the through passage in the first end 34 (FIGS. 7 and 8). The first end 34 of the needle assembly 33 is connected or connectable to the syringe 22 in removable manner.

Figure 6:
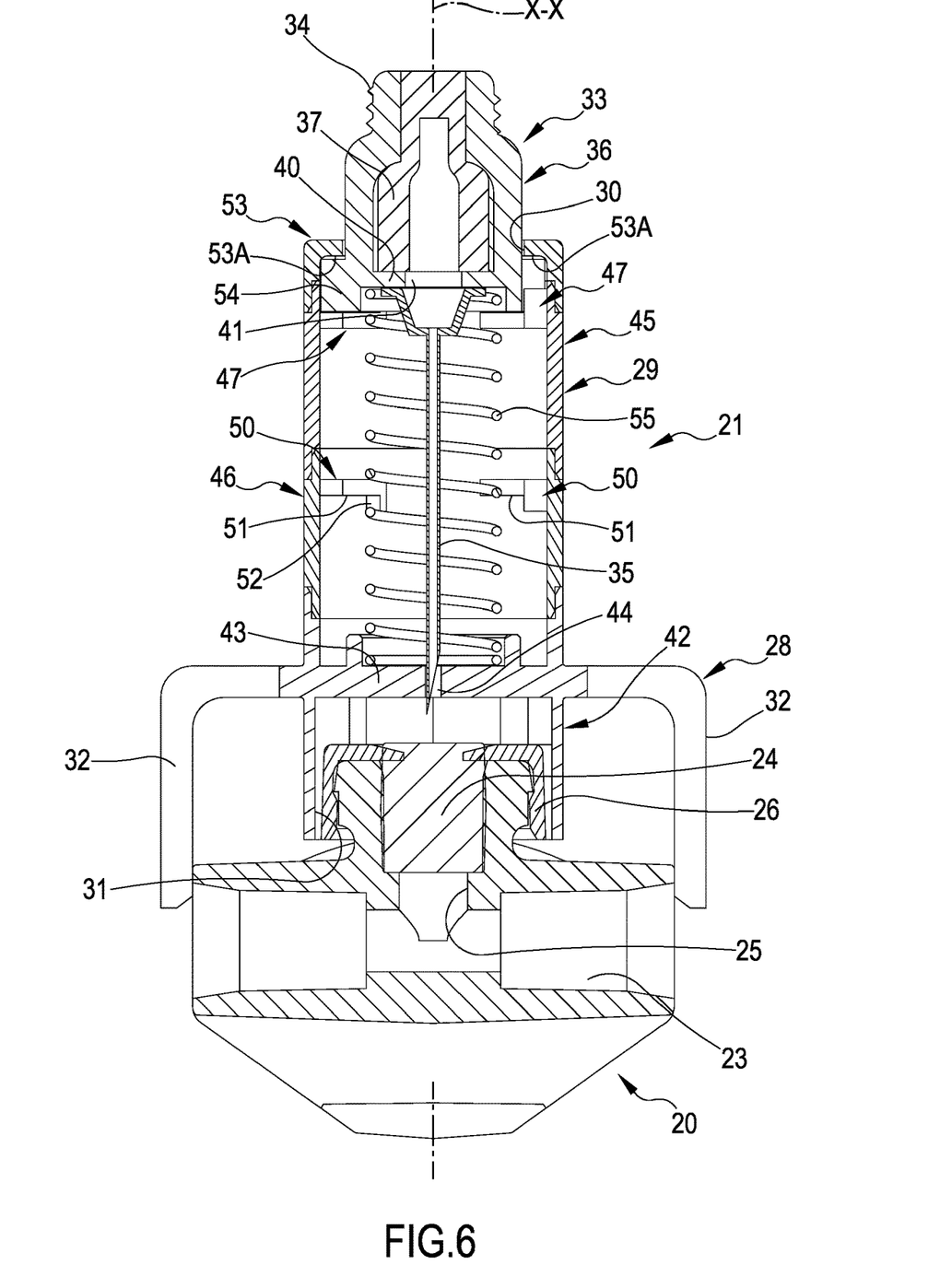
FIGS. 6, 7 and 8 each shows a sectional view of the fluid sampling or infusion assembly of FIG. 2 in a respective configuration.

The needle assembly 33 comprises a transverse wall 40 placed inside the tubular body 36, spaced from the first end 34 and having a hole 41. The transverse wall 40 is perpendicular to the main axis "X-X" and holds the valve 37 inside the tubular body 36. The valve 37 is a swabable valve which is partially accommodated in the through passage of the first end 34 and it is configured to open by the conical end 39 of the syringe 22 when said conical end 39 is inserted in the through passage (FIGS. 6, 7 and 8).

A proximal end of the needle 35 is joined to a side of the transverse wall 40 opposite the valve 37 and the needle 37 protrudes from the tubular body 34. The proximal end of the needle 35 is in fluid communication with the hole 41.

The needle assembly 33 is axially movable inside the protective body 29 between a first position and a second position. In the first position, the needle 35 is completely enclosed by the protective body 29 and the first end 34 of the needle assembly 33 protrudes from the first aperture 30 of the protective body 29 (FIGS. 6 and 7). In the second position, the needle 35 protrudes from the second aperture 31 of the protective body 29 to pierce the septum 24 of the sampling or infusion site 20 and the first end of the needle assembly 33 is placed inside the protective body 29 (FIG. 8).

The protective body 29 is made of four cylinders coaxially aligned along the main axis "X-X".

A lower cylinder 42 carries the connecting device 28 and delimits the second aperture 31. An interior wall 43 is perpendicular to the main axis "X-X", it is placed inside the lower cylinder 42 and has a through passage 44 for the needle 35.

A first middle cylinder 45 and a second middle cylinder 46 are superposed on the lower cylinder 42. The second middle cylinder 46 lies on the lower cylinder 42 and the first middle cylinder 45 lies on the second middle cylinder 46.

Figure 3:
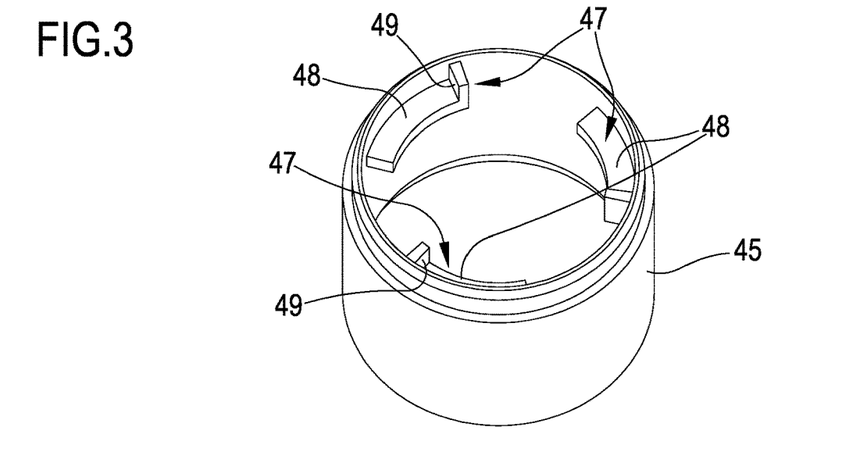
FIGS. 3, 4 and 5 each shows a respective element of the fluid sampling or infusion device of FIG. 2.
Figure 4:
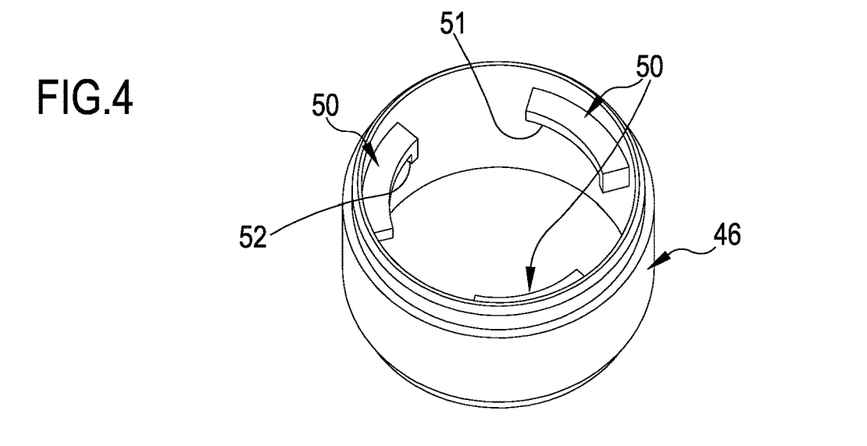
Figure 5:
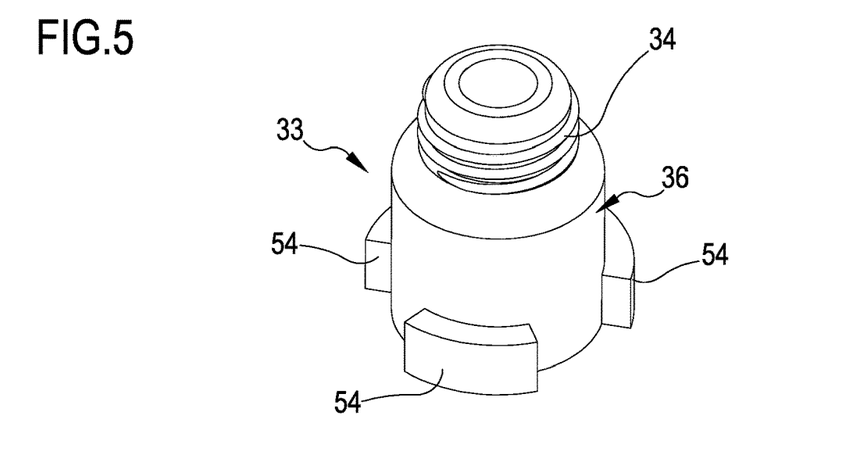

The first middle cylinder 45 comprises three first arch shaped relieves 47, protruding radially inside the first middle cylinder 45 and angularly spaced from each other (FIGS. 3, 6, 7 and 8). The first relieves 47 are disposed around the main axis "X-X" and are equidistant one from the other. Each first relief 47 has first arch shaped stop surface 48 perpendicular to an axial direction of movement of the needle assembly 33 and a second stop surface 49 perpendicular to a circumferential direction of the needle assembly 33 (FIG. 3). The second stop surface 49 is carried by a tooth of the first relief 47 placed at an extremity of the first arch shaped stop surface 48. The tooth projects from the first stop surface 48 towards the first aperture 30.

The second middle cylinder 46 comprises three second arch shaped relieves 50, protruding radially inside the second middle cylinder 46 and angularly spaced from each other (FIGS. 4, 6, 7 and 8).

The second relieves 50 are disposed around the main axis "X-X" and are equidistant one from the other. Each second relief 50 has first arch shaped stop surface 51 perpendicular to an axial direction of movement of the needle assembly 33 and a second stop surface 52 perpendicular to a circumferential direction of the needle assembly 33 (FIGS. 4, 6, 7, 8). The second stop surface 52 is carried by a tooth of the first relief 51 placed at an extremity of the first arch shaped stop surface 51. The tooth projects from the first stop surface 51 towards the second aperture 31.

An upper cylinder 53 is superposed on the first middle cylinder 45. The upper cylinder 53 delimits the first aperture 30 and has an annular surface 53A surrounding the first aperture 30 and facing the first relieves 47 of the first middle cylinder 45.

The tubular body 36 comprises three arch shaped lugs 54 projecting radially outward and angularly spaced from each other. Each lug 54 is shaped to pass between two first relieves 47 or between two second relieves 50 and to rest on the first stop surface 48 of the first relief 47 or on the first stop surface 51 of the second relief 50.

A helical spring 55 is operatively interposed between the protective body 29 and the needle assembly 33 and it is configured to push the needle assembly 33 towards the first position. The spring 55 surrounds the needle 35 and has a first extremity placed against a seat fashioned on the interior wall 43 and a second extremity placed against the needle assembly 33 (FIGS. 6, 7 and 8).

The three first arch shaped relieves 47 of the first middle cylinder 45 and the annular surface 53A of the upper cylinder 53 are part of a first blocker for the needle assembly 33. The three second arch shaped relieves 50 of the second middle cylinder 45 are part of a second blocker for the needle assembly 33. The first blocker is configured to block the needle assembly 33 in the first position and the second blocker is configured to block the needle assembly 33 in the second position.

Figure 2:
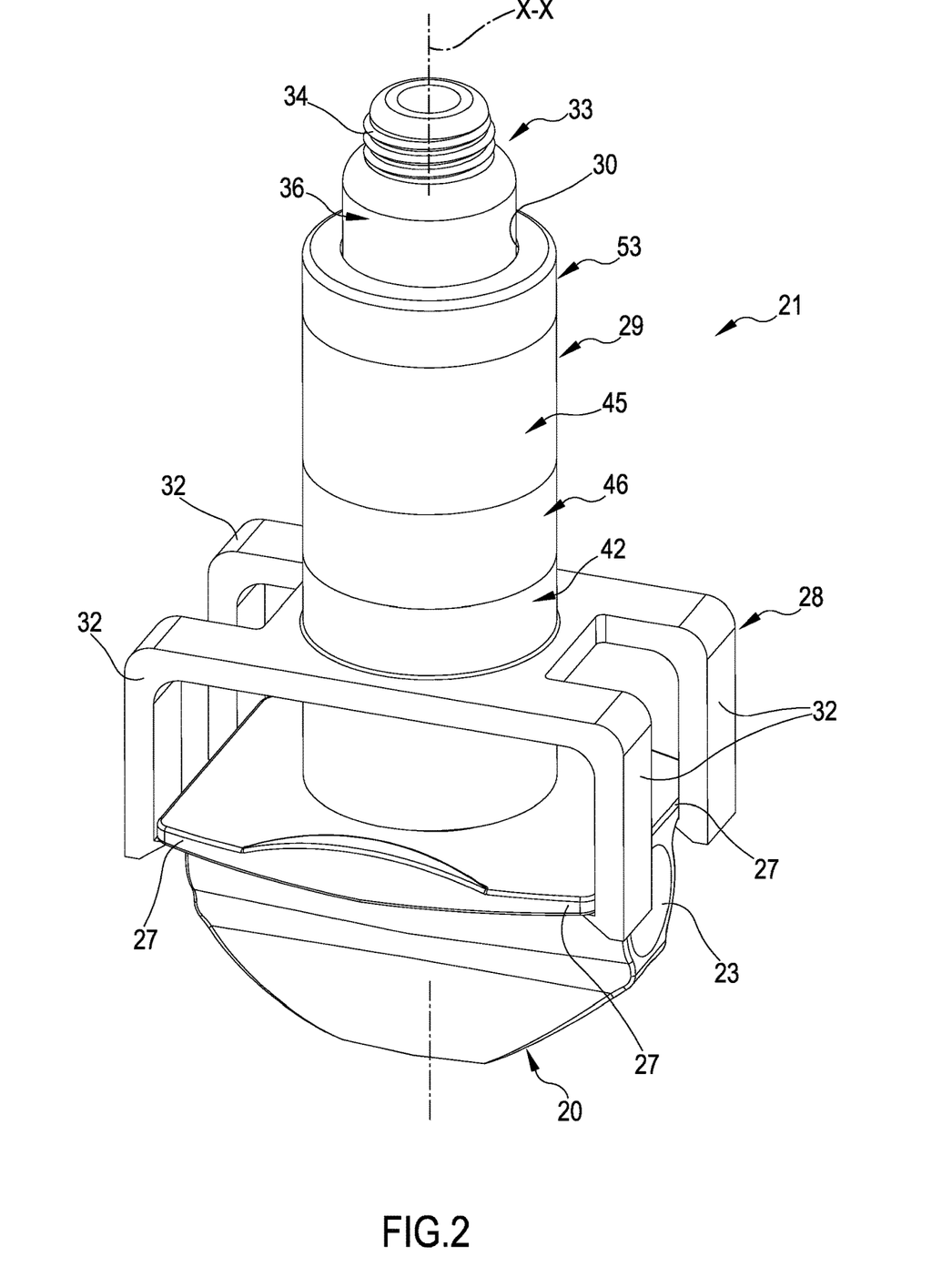
FIG. 2 shows a fluid sampling or infusion assembly according to the invention comprising a fluid sampling or infusion device and a sampling or infusion site.

In the first position, shown in FIGS. 2, 6 and 7, the three lugs 54 of the needle assembly 33 are axially placed between the annular surface 53A and the first relieves 50. The spring 55 pushes the needle assembly 33 against the annular surface 53A. The annular surface 53A prevents the needle assembly 33 from coming out of the protective body 29.

A first angular position of the needle assembly 33 with respect to the protective body 29 is such that each lug 54 faces the first stop surface 48 and lies against the second stop surface 49 of one of the first relieves 47. This way, the first blocker prevents an axial displacement of the needle assembly 33. Indeed, an axial pressure exerted on the needle assembly 33 pushes the needle assembly 33 against the first stop surfaces 48 but the needle assembly 33 cannot move axially. Furthermore, the second stop surfaces 49 prevents a clockwise rotation of the needle assembly 33 with respect to the protective body 29.

In the first position, the needle assembly 33 can be rotated counter clockwise from the first angular position to a second angular position. In the second angular position, each lug 54 faces a space delimited by two first relieves 47. The spring 55 keeps on pushing the needle assembly 33 against the annular surface 53A but an axial pressure exerted on the needle assembly 33 may cause an axial displacement of the needle assembly 33 towards the second aperture 31 in contrast to the elastic force of the spring 55. Indeed, each lug 54 is free to pass through the space delimited by two first relieves 47. When the needle assembly 33 is in the second angular position, the teeth of the first relieves 47 prevent a further counter clockwise rotation of the needle assembly 33.

When the needle assembly 33 is in the first position and in the first angular position, the syringe 22 can be screwed on the first end 34 of needle assembly 33 through a clockwise rotation. When the needle assembly 33 is in the first position and in the second angular position, the syringe 22 can be unscrewed from the first end 34 of needle assembly 33 through a counter clockwise rotation.

Once the syringe 22 is screwed on the first end 34, the needle assembly 33 is rotated counter clockwise to the second angular position and then moved axially towards the second aperture 31 until the three lugs 54 pass through the spaces delimited by the second relieves 50 and beyond said second relieves 50.

Then the needle assembly 33 is in the second position and can be rotated clockwise again towards the first angular position, in which the three lugs 54 rest against the teeth of the second relieves 50.

When the needle assembly 33 is in the second position and in the first angular position, the second relieves 50 prevent an axial displacement of the needle assembly 33 towards the first aperture 30 and the first position and prevents also a further clockwise rotation of the needle assembly 33. Indeed, the spring 55 pushes the needle assembly 33 against the first stop surfaces 51 of the second relieves 50 but the needle assembly 33 cannot move axially. When the needle assembly 33 is in the second position and in the first angular position, the needle 35 is kept inside the septum 24 and inside the stretch of tubing 23 (FIG. 8). The user can pull the plunger of the syringe 22 to extract a fluid sample or can push the plunger to inject a fluid while the needle 35 is stationary inside the sampling or infusion site 20.

Once the sample has been extracted or injected, the needle assembly 33 is rotated counter clockwise to the second angular position in which a further counter clockwise rotation of the needle assembly 33 is prevented but the axial displacement is allowed. The spring 55 pushes the needle assembly 33 towards the first position and causes an automatic extraction of the needle 35 from the septum 24 and retraction of said needle 35 inside the protective body 29. The spring 55 is a mechanism for automated needle retraction. These features, and optionally also the friction of the needle assembly 33 against the second blocker, are such that the syringe 22 cannot be disconnected from the needle assembly 33 without being automatically extracted. This enables preventing situation where the needle 22 would remain in sampling or infusion position when treatment is resumed, resulting in risk of haemolysis.

In other embodiments, the clockwise and counterclockwise blocks and/or rotations of the needle assembly 33 may be also reversed if the screwing and unscrewing directions of the syringe 22 are reversed.

The fluid sampling or infusion device 21 and the sampling or infusion site 20 above described may be part of a fluid sampling or infusion assembly which may also comprise the syringe 22. The fluid sampling or infusion device 21 may be disposable.

According to a sampling or infusion method that uses the fluid sampling or infusion device 21 and the sampling or infusion site 20 above described, the fluid sampling or infusion device 21 is first connected to the sampling or infusion site 20 through the connecting device 28. Then the syringe 22 is connected to the first end 34 of the needle assembly 33 while the needle assembly 33 is in the first position and in the first angular position. The needle assembly 33 is rotated in the second angular position and then the syringe 22 and the needle assembly 33 are pushed towards the second position to pierce the septum 24 of the sampling or infusion site 20. The needle assembly 33 is rotated to the first angular position to block the needle in the sampling or infusion site 20 and a fluid sample is extracted or injected through the syringe 22. After sample extraction or injection, the needle assembly 33 is rotated to the second angular position and the needle is automatically extracted from the septum 24. The syringe 22 may be unscrewed from the needle assembly 33 and the sampling or infusion device 21 is disconnected from the sampling or infusion site 20.

The fluid sampling or infusion device 21 above described together with the blood treatment unit 2, the blood withdrawal line 6, the blood return line 7 and at least one sampling or infusion site 20 comprising a stretch of tubing mounted and in fluid communication with the blood withdrawal line 6 or the blood return line 7 may be part of a disposable extracorporeal blood treatment set.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and the scope of the appended claims.

The invention claimed is:

1. A fluid sampling or infusion device comprising:
a protective body including a first aperture and a second aperture, the protective body comprising a connecting device configured to connect, in a removable manner, the protective body to a sampling or infusion site;

a needle assembly comprising a first end connectable in a removable manner to a syringe, and a needle protruding from a second end opposite the first end;

wherein the needle of the needle assembly is movable relative to the protective body at least between a first position and a second position inside the protective body, and wherein at least the needle of the needle assembly is inside the protective body;

wherein in the first position the needle is completely enclosed by the protective body; and wherein in the second position at least a part of the needle protrudes from the second aperture of the protective body to allow piercing the sampling or infusion site.

2. The device of claim 1, wherein the needle assembly is movable as a whole inside the protective body at least between the first position and the second position.

3. The device of claim 1, wherein, at least in the first position, the first end of the needle assembly protrudes from the first aperture of the protective body, and in the second position, the first end of the needle assembly is placed inside the protective body.

4. The device of claim 1, comprising a first blocker operatively interposed between the needle assembly and the protective body and placed adjacent to the first aperture, wherein the first blocker is configured to block the needle assembly in the first position, wherein in the first position, the needle assembly is movable with respect to the first blocker between a first angular position and a second angular position, wherein in the first angular position the first blocker prevents an axial displacement of the needle assembly, and wherein in the second angular position the first blocker allows an axial displacement of the needle assembly towards the second aperture.

5. The device of claim 4, wherein when the needle assembly is in the first angular position, the first blocker is configured to prevent a clockwise rotation of the needle assembly and, when the needle assembly is in the second angular position, the first blocker is configured to prevent a counter-clockwise rotation of the needle assembly.

6. The device of claim 4, wherein when the needle assembly is in the first angular position, the first blocker is configured to prevent a counter-clockwise rotation of the needle assembly and, when the needle assembly is in the second angular position, the first blocker is configured to prevent a clockwise rotation of the needle assembly.

7. The device of claim 4, wherein the first blocker comprises one or more first relieves protruding radially inside the protective body and angularly spaced from each other, the first relieves being arch-shaped.

8. The device of claim 7, wherein the first blocker comprises an annular surface facing a first relief of the one or more first relieves and spaced from said first relief to accommodate a lug of the needle assembly between said annular surface and the first relief, wherein the annular surface is an internal surface of the protective body and surrounds the first aperture of said protective body.

9. The device of claim 7, wherein each of the first relieves comprises a first stop surface perpendicular to an axial direction of movement of the needle assembly and a second stop surface perpendicular to a circumferential direction of the needle assembly.

10. The device of claim 1, comprising a second blocker operatively interposed between the needle assembly and the protective body and spaced from the first aperture, wherein the second blocker is configured to block the needle assembly in the second position, wherein in the second position, the needle assembly is movable with respect to the second blocker between a first angular position and a second angular position, wherein in the first angular position the second blocker prevents an axial displacement of the needle assembly towards the first aperture, and wherein in the second angular position the second blocker allows an axial displacement of the needle assembly towards the first aperture.

11. The device of claim 10, wherein when the needle assembly is in the first angular position, the second blocker is configured to prevent a clockwise rotation of the needle assembly, and when the needle assembly is in the second angular position, the second blocker is configured to prevent a counter-clockwise rotation of the needle assembly, or wherein when the needle assembly is in the first angular position, the second blocker is configured to prevent a counter-clockwise rotation of the needle assembly, and when the needle assembly is in the second angular position, the second blocker is configured to prevent a clockwise rotation of the needle assembly.

12. The device of claim 7, comprising one or more lugs projecting radially outward and configured to engage the first blocker or a second blocker, the second blocker comprising one or more arch-shaped second relieves, wherein the one or more lug is shaped to pass between two first relieves or between two second relieves.

13. The device of claim 1, comprising a mechanism for automated needle retraction from the second position towards the first position, wherein the mechanism for automated needle retraction comprises a spring operatively interposed between the protective body and the needle assembly, and wherein the mechanism for automated needle retraction is configured to push the needle assembly towards the first position.

14. The device of claim 13, wherein the protective body comprises a through passage for the needle, and an interior wall located adjacent to the second aperture, wherein the spring includes a first extremity placed against the interior wall and a second extremity placed against the needle assembly, and wherein the spring surrounds the needle.

15. The device of claim 1, wherein the first end of the needle assembly includes a thread configured to engage a thread of a tip of the syringe.

16. The device of claim 1, wherein the needle assembly comprises a tubular body that includes the first end, wherein a proximal end of the needle is mounted inside the tubular body and at least a distal tip of the needle protrudes from the tubular body.

17. The device of claim 16, wherein the needle assembly comprises a swabable valve mounted inside the tubular body and placed at the proximal end of the needle, wherein the needle assembly comprises a transverse wall placed inside the tubular body, the transverse wall including a hole closed by a valve.

18. The device of claim 1, wherein the connecting device includes a clip fastener that comprises elastic arms protruding from the protective body, and wherein the connecting device is configured to engage one or more tabs of the sampling or infusion site.

19. The device of claim 1, wherein the protective body includes a main axis, and wherein the needle is movable along the main axis between the first position and the second position.

20. The device of claim 1, wherein the protective body and the connecting device are fixed relative to one another, and wherein the needle and the needle assembly move inside a housing defined by the protective body.

21. The device of claim 1, wherein the needle assembly comprises a valve and a tubular body that includes the first end,
   wherein the first end includes an external thread configured to engage a thread of a tip of the syringe,
   wherein a proximal end of the needle is mounted inside the tubular body and at least a distal tip of the needle protrudes from the tubular body,
   wherein a conical end of the tip of the syringe is configured to enter a through passage in the first end,
   wherein the first end of the needle assembly is a female Luer lock, and
   wherein the needle assembly is mounted inside the tubular body and placed at the proximal end of the needle.

22. The device of claim 21, wherein the needle assembly comprises a transverse wall placed inside the tubular body, the transverse wall including a hole,
   wherein the valve is accommodated between the transverse wall and the first end of the needle assembly to open or close the hole, and
   wherein the proximal end of the needle is joined to the transverse wall and in fluid communication with the hole.

23. The device of claim 1, wherein the first end of the needle assembly is in fluid communication with the needle, the needle assembly including a valve configured to selectively inhibit fluid communication between the external environment and an end of the needle connected to the second end of the needle assembly.

24. The device of claim 1, wherein the protective body further includes a lower cylinder carrying the connecting device and delimiting the second aperture, and wherein when connected to the infusion site, the lower cylinder embraces an emerging portion of the infusion site housing a pierceable septum.

25. A fluid sampling or infusion assembly for an extracorporeal blood treatment apparatus comprising:
   a fluid sampling or infusion device including:
      a protective body including a first aperture and a second aperture, the protective body comprising a connecting device configured to connect, in removable manner, the protective body to a sampling or infusion site, and
      a needle assembly comprising a first end connectable in removable manner to a syringe and a needle protruding from a second end opposite the first end,
      wherein the needle of the needle assembly is movable with respect to the protective body at least between a first position and a second position inside the protective body, and wherein at least the needle of the needle assembly is inside the protective body,
      wherein in the first position the needle is completely enclosed by the protective body, and
      wherein in the second position at least a part of the needle protrudes from the second aperture of the protective body to allow piercing the sampling or infusion site; and
   a sampling or infusion site comprising a length of tubing in fluid connection with the extracorporeal blood treatment apparatus or a part of the extracorporeal blood treatment apparatus.

26. The fluid sampling or infusion assembly of claim 25, wherein the sampling or infusion site comprises the length of tubing, a septum, and at least a tab configured to be engaged by the connecting device, and
   wherein the septum closes a side access to the length of tubing and is configured to be pierced by the needle of the fluid sampling or infusion device.

27. The fluid sampling or infusion assembly of claim 26, wherein the sampling or infusion site comprises a cap surrounding the septum, and wherein the cap is configured to be engaged by the second aperture of the protective body when the connecting device of the protective body is connected to the sampling or infusion site.

28. The fluid sampling or infusion assembly of claim 25, comprising a syringe having a tip connected or connectable to the first end of the needle assembly, wherein the tip of the syringe comprises an inner threaded cylindrical body and a conical end placed inside the inner threaded cylindrical body, the conical end including a syringe opening.

* * * * *